United States Patent [19]

Gelabert

[11] Patent Number: 5,041,099
[45] Date of Patent: * Aug. 20, 1991

[54] NON-REUSABLE SYRINGE AND CAP THEREFOR

[76] Inventor: Danilo D. Gelabert, 314 McBrien Rd., Apt. 815, Chattanooga, Tenn. 37411

[*] Notice: The portion of the term of this patent subsequent to Mar. 20, 2007 has been disclaimed.

[21] Appl. No.: 488,667

[22] Filed: Mar. 5, 1990

Related U.S. Application Data

[63] Continuation-in-part of Ser. No. 245,797, Sep. 16, 1988, Pat. No. 4,909,795.

[51] Int. Cl.$^5$ ............................................... A61M 5/32
[52] U.S. Cl. ...................................... 604/192; 604/263
[58] Field of Search ......................... 604/192, 263, 187

[56] References Cited

U.S. PATENT DOCUMENTS

| | | | |
|---|---|---|---|
| 3,434,473 | 3/1969 | Smith | 604/192 |
| 4,735,311 | 4/1988 | Lowe et al. | 604/263 X |
| 4,826,488 | 5/1989 | Nelson et al. | 604/192 |

FOREIGN PATENT DOCUMENTS 229204  7/1987  European Pat. Off. ............ 604/263

Primary Examiner—John D. Yasko
Attorney, Agent, or Firm—Alan Ruderman

[57] ABSTRACT

A non-resuable syringe has inner and outer barrels including a needle connected by hub to the inner barrel and a plunger attached to the outer barrel and received within the inner barrel. A pair of circumferentially adjacent longitudinally extending tracks in the form of teeth are on the outer surface of the inner barrel and a traveler is fixed to the inner surface of the outer barrel, the teeth being such that the traveler may ride on each track in only one direction. The outer barrel may be rotated to move the traveler from an outgoing track for charging the syringe to an incoming track for discharging the syringe, but the teeth on the outgoing track have a greater height than the teeth on the incoming track so that the traveler cannot move back onto the outgoing track. The hub has a flange including an inclined needle facing surface. A protective cap having a skirt at the open end may be disposed on the hub with the skirt removeably positioned on the flange. Another flange on the skirt has the same configuration as the flange on the hub, and after the use of the syringe the cap and hub are pushed together until the flanges lock to preclude removal of the cap. The cap has three feet at the closed end so it may be stood upright while the syringe is being used thereafter permitting insertion of the needle into the cap while eliminating inadvertent pricking. The feet may be resiliently joined to the body of the cap for packing purposes.

8 Claims, 1 Drawing Sheet

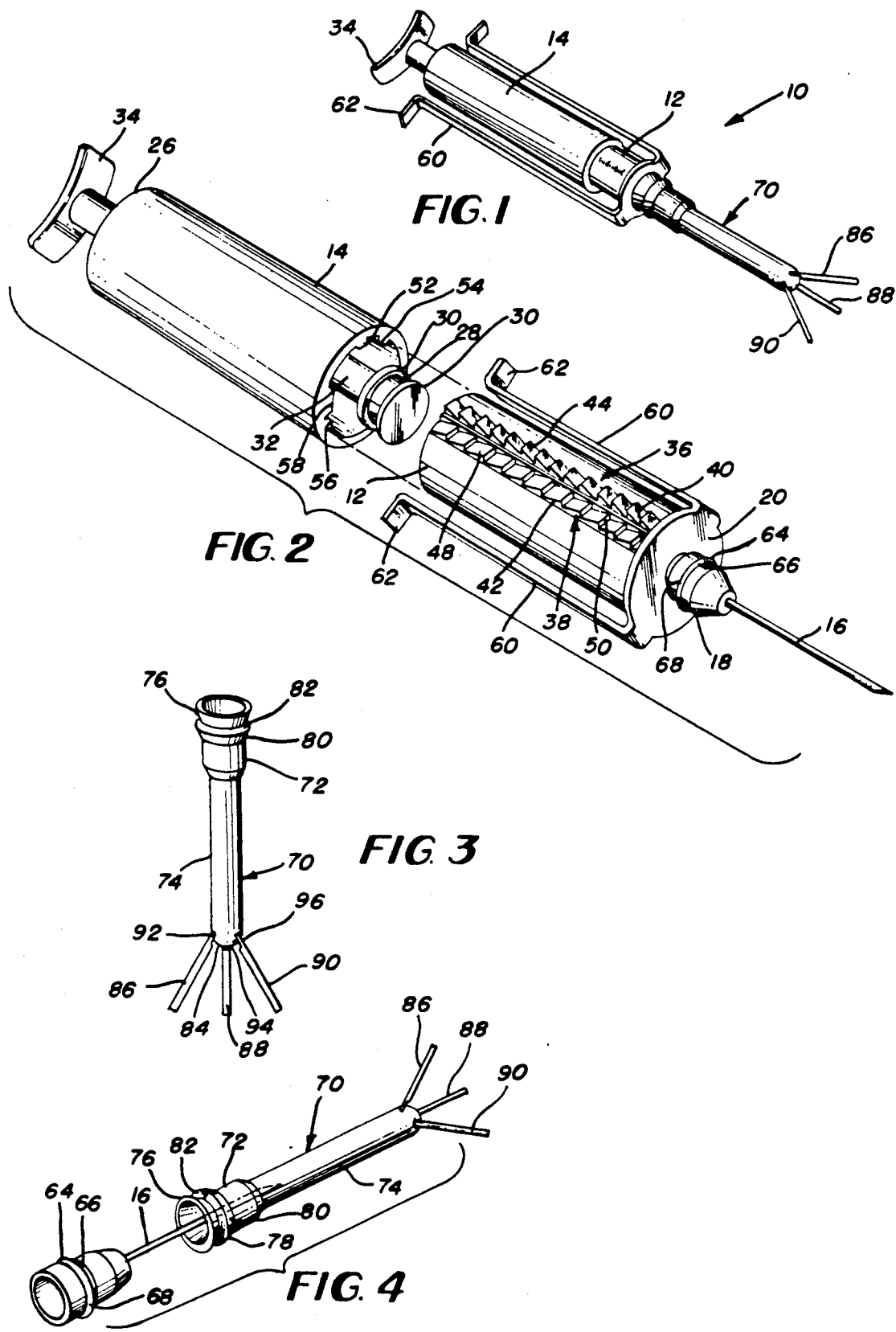

NON-REUSABLE SYRINGE AND CAP THEREFOR

REFERENCE TO RELATED APPLICATIONS

This application is a continuation-in-part of copending application Ser. No. 245,797 filed Sept. 16, 1988, now U.S. Pat. No. 4,909,795 issued Mar. 20, 1990.

BACKGROUND OF THE INVENTION

This invention relates to hypodermic syringes and more particularly to a hypodermic syringe having a protective cap which can be used only one and which may be locked over the needle after the syringe has been used to preclude reuse of the syringe.

With the increase of drug addiction by the intravenous injection of drugs in today's society, and the growth of certain health destroying diseases such as hepatitis and AIDS, which can be transmitted by the multiple use of syringes, it is highly desirable that hypodermic syringes be used only once and either destroyed or discarded in such a state that they are not reusable. Separate devices for destroying a syringe after use involves severing the needle and barrel components and results in the inconvenience of the additional acts of placing the syringe in the device and activating such device. If the syringe is not immediately destroyed in such a device but awaits personel to perform the act, the syringe may escape the normal procedure and be displaced before destruction can occur. Thus, a substantial number of non-reusable syringes have been proposed in the art in recent years.

In my aforesaid copending patent application I have disclosed a non-reusable syringe having a plunger attached to and moveable with an outer barrel, the plunger being received within an inner barrel, and wherein one of the barrels has a pair of longitudinally extending tracks and the other of the barrels has a traveler. The tracks are formed so that the relative movement between the traveler and each track is possible in only one longitudinal direction so that the outer barrel and the plunger may be drawn away from the needle at the end of the inner barrel to charge the inner barrel when the traveler is on one track. Relative rotation of the barrels thereafter drops the traveler onto the other track to permit the plunger to be moved to discharge the inner barrel. Also disclosed is a syringe and a protective cap for use therewith, the syringe having a needle mounting hub including a cam flange on the periphery thereof spaced from the needle end. The cap is positionable on the hub and has a skirt at the open end for receiving the cam flange prior to use of the needle and being removeable therefrom when the syringe is in use. The cap additionally includes an annular cam adjacent the skirt adapted to cooperatively receive the cam flange when the skirt is forced over the cam flange after the syringe has been used but precludes withdrawal of the cam flange thereafter. Thus, the syringe and cap are constructed to permit the cap to be positioned on the hub of the syringe for subsequent removal so that the syringe can be used, and includes a construction which after use of the syringe locks the cap onto the syringe precluding reuse thereof.

Although the apparatus disclosed in the aforesaid patent application provides advantages over the prior art, studies have indicated that most accidental and inadvertent needle pricks result during recapping of a needle. It appears that this may be the main reason why most medical treatment facilities do not re-cap before their disposal even those which may possibly contain infectious diseases. This practice in failing to follow precautionary re-capping procedures makes it possible to reuse a needle whether inadvertently or by one seeking a needle for illegal use. Additionally, a nonrecapped needle can readily result in accidental pricking as a needle goes through the disposal process.

All the prior art known to the Examiner is disclosed in the aforesaid patent application and in two references cited during the prosecution of that application. The only known art relating to a needle cap is thus disclosed in Lesson et al U.S. Pat. No. 3,890,971 where a plunger and needle cap may be permanently locked after use; in Geiger U.S. Pat. No. 4,121,588 which has a weakened zone for breaking the barrel of the syringe so that the needle stays in the cap; and in the art cited in the aforesaid application.

SUMMARY OF THE INVENTION

Consequently, it is a primary object of the present invention to provide a cap which can be locked onto a syringe after use, the cap having means for positioning the cap in an upright position with the open end of the cap readily disposed for insertion of the needle of the syringe after use.

It is a further object of the present invention to provide a cap which is positionable over the needle of a syringe and lockable thereon after the needle has been used, the cap having feet disposed at its closed end, the feet permitting the cap to freely stand on a horizontal surface so that after use of the syringe the needle may be readily positioned within the cap with one hand so as to thereby preclude the possibility of an accidental pricking.

It is a still further object of the present invention to provide a syringe including a needle mounting hub having a cam flange on the periphery thereof spaced from the needle end, and a protective cap positionable on the hub, the cap having a skirt at the open end for receiving the cam flange prior to use of the needle and removeable therefrom when the syringe is in use, the cap further including an annular cam adjacent the skirt adapted to cooperatively receive the cam flange when the skirt is forced over the cam flange after the syringe has been used, but to preclude withdrawal of the cam flange therefrom, the cap additionally having feet at the closed end so that the cap may be positioned upright on a table or the like permitting the needle to readily inserted therein.

Accordingly, the present invention provides a needle and a protective cap for use with a syringe, the needle having a hub secured thereto for attachment to the barrel of a syringe, and a protective cap positionable on the hub for subsequent removal permitting the syringe to be used, while also including means for subsequently locking the cap onto the syringe to preclude reuse of the syringe. The cap includes a plurality of feet at the closed end which permits the cap to stand in an upright position on a table or the like so that the needle can be inserted into the cap and locked without jeopardizing the safety of the professional applying the syringe. Once the cap has been locked onto the hub, the needle is rendered safe from inadvertent and accidental pricking.

In the specific form of the invention the hub of the syringe to which the needle is secured includes a flange on the periphery in the form of a cam having a sloped surface at the needle facing end and a step at the opposite end. The protective cap has a correspondingly configured skirt at the open end for positioning on the cam flange prior to use of the syringe for protecting the needle. The cap also has an annular flange on its periphery spaced from the skirt, and the flange has the same configuration as the cam flange on the hub. The cap additionally includes a plurality of feet at the closed end. The cap may be readily removed from its protective position, and stood in an upright position. After use of the syringe, the syringe is positioned so that the needle is inserted into the cap, and pushed so that the cap be positioned over the hub until the flange on the hub is seated within the annular flange of the cap. After it is so seated, the cap cannot be removed from the hub so that it maintains its protective condition with the needle.

Another aspect of the invention is the provision of providing a living hinge at the connection between the feet and the cap so that the feet may be folded inwardly within the envelope of the diameter of the cap so as to minimize the packaging and storage space required for the feet.

BRIEF DESCRIPTION OF THE DRAWINGS

The particular features and advantages of the invention as well as other objects will become apparent from the following description taken in connection with the accompanying drawings, in which:

FIG. 1 is a perspective view of a syringe and cap constructed in accordance with the principles of the present invention;

FIG. 2 is an exploded perspective view of the syringe illustrated in FIG. 1 showing the major components thereof;

FIG. 3 is a perspective view of the protective cap of the present invention in an upstanding position on the feet; and FIG. 4 is a perspective view of a protective cap for use with a syringe needle and showing the needle in phantom.

DESCRIPTION OF THE PREFERRED EMBODIMENTS

Referring now to the drawings, a syringe 10 constructed in accordance with the preferred embodiment of the present invention is disclosed as having an inner barrel 12 and an outer barrel 14, both barrels being of generally cylindrical form, and preferably constructed from appropriate thermoplastic material with at least the inner barrel being transparent.

The inner barrel 12 has a hollow interior which communicates with a hollow needle 16 at the forward end, the needle 16 being attached to a plastic hub 18 and either extending therethrough into communication with the interior of the barrel 12 or opening onto the hub 18 with the hub communicating with the interior of the barrel. In either case the hub may be fixed to or removeably attached to the front end 20 of the inner barrel 12 with the opposite end 22 of the inner barrel being open.

The outer barrel 14 is open at its front end 24 and has a hollow interior of a diameter slightly larger than the outer diameter of the inner barrel 12, the rear end 26 of the barrel 14 being closed. The barrel 14 includes a plunger 28 mounted substantially concentric with the interior thereof and may extend from the front end 24. The plunger 28 is a substantially cylindrical member which may be of an elastomeric material or preferably is formed of a thermoplastic and includes elastomeric seals 30 which are compressively received within the hollow interior of the outer barrel 12 in sealed relationship with the interior wall thereof as illustrated in FIG. 3. Thus, the plunger 28 is disposed within the inner barrel 12 while the inner barrel is disposed within the outer barrel. The plunger 28 may be secured to the outer barrel 14 by means of a rod 32 attached at the rear face of the plunger and extending to the closed rear end 26 of the barrel 14. The rod 32 may extend through the rear end 26 which would then be closed about the extending portion, or another rod may extend from the rear face of the closed end 26. In either instance an operator or gripping member 34 is attached to the extending rod for drawing the outer barrel 14 and plunger 28 rearwardly relative to the inner barrel 12 during the charging stroke and for pushing the outer barrel 14 and plunger 28 forwardly during the discharge stroke as hereinafter described.

A pair of longitudinally extending tracks are disposed on or recessed from the outer periphery of the inner barrel or the inner periphery of the outer barrel while a traveler or track rider is disposed on the other of the barrels. In the preferred form of the invention, and for purposes of illustration, the tracks are disposed on the outer periphery of the inner barrel 12 while the traveler projects from the inner periphery of the outer barrel 14. Thus, tracks 36 and 38 extend longitudinally along the periphery of the barrel 12 and extend from adjacent the front end 20 to the rear end 22, the tracks 36 and 38 being circumferentially spaced apart but adjacent one another.

The track 36 is the outgoing or charging track while the track 38 is the incoming or discharge track. As illustrated, each of the tracks 36, 38 comprise a series of teeth 40, 42 respectively extending substantially radially from the periphery of the barrel 12 with each of the teeth having a sloped surface and a step. The sloped surface 44 of the teeth 40 are inclined upwardly from the periphery of the barrel 12 in the direction from the front end 20 toward the rear end 22, and each tooth 40 has a step or riser 46 at the trailing end thereof which drops downwardly toward the periphery of the barrel 12 at which point the adjacent tooth commences. Thus, the teeth 40 are effectively detents providing a one-way rack or ratchet bar. The teeth 42 of the track 38 are also one-way rack or ratchets but, on the other hand, has the sloped surface 48 inclined upwardly from the periphery of the barrel in the direction from the rear end 22 toward the front end 20 with each step or riser 50 also at the trailing end, the trailing end in this case being at the front of the barrel. Thus, the risers 46 of the teeth 40 face the rear end of the barrel 12, while the risers 50 of the teeth 42 face the front end 20 of the barrel 12. Additionally, the height of the teeth 42 above the periphery of the barrel 12 is less than the height of the teeth 40, as best illustrated in FIGS. 4 and 5, for purposes which will hereinafter become clear.

Disposed within the barrel 14 on the inner wall thereof at the front end is a traveler in the form of a protuberence 52. The traveler 52 projects radially inwardly toward the center of the barrel 14 by an amount such that it engages the sloped surface 48 of the teeth 42 at the radially innermost portion thereof, i.e., the edge of the teeth 42 which abut the riser 50 at the trailing edge. The traveler may thus ride over the teeth 42 on the discharge stroke readily without stress thereof, and when initially positioned on the teeth 40, as hereinafter described, the traveler will be stressed in compression, as may the teeth 40 and the barrel 12. Also formed on the inner wall of the barrel 14 is an abutment or stop member 54 also in the form of a radially extending protuberence, the abutment member 54 being disposed such that the outer barrel 14 may be rotated relative to the inner barrel 12 when the traveler is disposed on the teeth 40 of the track 36 in the direction to move the traveler onto the track 38, but once the traveler is on the teeth 42 of the track 38, rotation in that same direction is precluded by the abutment member 54 acting against the teeth 40 of the track 36. Thus, the traveler may be switched from track 36 to track 38, but cannot be switched from track 38 to track 36. At least one and preferably two other protuberences 56, only one of which is illustrated, may extend radially from the interior wall of the outer barrel 14 for maintaining concentric alignment of the barrels 12 and 14.

As illustrated in FIG. 2, the teeth 40 and 42 of the respective tracks 36 and 38 are offset slightly from each other. Additionally, an assembly stop boss 58 extends from the interior wall of the outer barrel 14, the assembly boss being circumferencially spaced from the traveler 52 in the direction in which the traveler is to be moved from the track 36 onto the track 38. The circumferencial disposition of the traveler 52, the stop member 54 and the assembly stop boss 58 is such that the outer barrel 14 may be positioned about the inner barrel 12 during initial assembly with the assembly stop boss 58 disposed on the teeth 42 of the low track 38 so that the traveler is disposed adjacent the teeth 40 of the high track 36 on the remote side of the track 38. The assembly stop boss protrudes from the outer barrel an amount such that it compresses the teeth 42 of the track 36 when so positioned thereon, i.e., there is a preloading force applied by the assembly stop boss on the teeth 42. The assembly stop boss 58 prevents relative rotation of the barrels 12, 14 in the direction opposite to the direction the traveler must be moved to enter onto the track 38 from the track 36. The outer barrel may then be pushed in relatively to the inner barrel 12 with the assembly stop boss riding on the teeth 42 of the low track, and with the traveler moving freely. When the plunger 28 is then seated adjacent the wall 20 of the closed end of the inner barrel 12, the traveler is adjacent the lower portion of the slope 44 of the first tooth 40, i.e., the tooth 40 most adjacent the front wall 20. The barrels 12, 14 may then be relatively rotated slightly until the traveler 52 is disposed on the first tooth 40 of the high track 36, and the assembly stop boss 58 is at that time displaced from the low track 38 on the side thereof remote from the track 36. The assembly boss thereafter prevents the barrels from rotating in the direction which would dislodge the traveler from the high track 36 toward the remote side of the track 38. If desired or found necessary, a protuberence or enlargement may be placed in the front of the tooth 42 adjacent that front tooth 40 so that the relative rotation of the barrels is limited to ensure that the traveler stops on and does not overshoot the tooth 40 of the charging track. Once so positioned the syringe is ready for use.

A pair of elongated limbs 60 extending at opposed circumferencial portions of the front wall of the barrel 12 have respective grasping flanges 62, the limbs 60 being disposed about the outer barrel 14 when assembled so that the flanges 62 aid in the pulling back and subsequent pushing forward of the outer barrel 14 relative to the inner barrel 12. A description of the operation of the syringe for precluding reuse may be had by reference to the aforesaid patent application.

In accordance with the present invention, the needle hub 18, which may be removably attached to the syringe body by conventional means such as threads or the like, has a flange 64 extending radially outwardly from the surface thereof. The flange 64 may extend continuously about the circumference of the hub as illustrated or there merely may be a pair of diametrically opposed flanges extending therefrom. The flange 64 has a forward facing sloped surface 66 which slopes outwardly and radially so that the rear of the flange is at the greatest extent from the surface of the hub, thereby forming a sharp step 68 at the rear of the flange 64. A protective cap 70 having an enlarged diametric portion 72 for fitting over the hub 18 and an elongated narrow smaller diameter portion 74 for fitting about the needle in protective conventional manner is provided, the cap 70 having a first annular flange or skirt 76 adapted to receive the entire flange 64 of the hub 18. The skirt 76 has the same configuration as the flange 64 and may be positioned snugly thereon prior to use and may be removeable therefrom by pulling the cap forwardly when the syringe is ready for use. The cap 70 also has another annular flange 78 spaced from the skirt 76, the flange 78 being of the same configuration as the flange 64 on the hub. Thus, the annular flange 78 has a sloped surface 80 sloping upwardly and rearwardly from the surface of the portion 72 to a point where it has a sharp drop or step 82. After use of the syringe, the cap may be pushed, as hereinafter described, over the needle 16 and the hub 18 until the flange 64 is received within the annular flange 78 and the steps 68 and 82 abut. Thereafter, the cap 70 is locked to the hub 18 since the steps preclude removal of the cap from the hub. Accordingly, access to the needle is prevented, whether or not the needle hub is separatable from the syringe body.

In order to overcome the problem of recapping the needle after it has been used to avoid accidental and inadvertent pricking, the cap 70 of the present invention at the closed end 84, i.e., the end remote from the skirt 76, has support means, in the form of feet 86, 88, 90 for permitting the cap to be disposed in an upright position as illustrated in FIG. 3. Preferably there are three such feet which extend outwardly from the closed end and at an inclination thereto and to each other so that they act as a tripod and provide a stable support when positioned on a table or other planar surface. Thus, the cap may stand freely on its own on such a surface. The specific size and configuration of the feet is not critical. They may be of a constant cross sectional configuration or taper, and it is anticipated that the length of each foot would be in the order of approximately ½ to ¾ of an inch, but again this is not critical since the only purpose of the feet is to support the cap with the open end extending upwardly while the syringe is in use so that easy insertion of the needle into the cap after use of the syringe is available. Thus, all that is necessary to use and recap the needle is to remove the cap, stand the cap on the feet 86, 88, 90, use the syringe to dispense the medicant, and then position the syringe for insertion of the needle vertically into the hollow of the cap and push the syringe downwardly until the flange 64 of the hub 18 is received within the annular flange 78 with the steps 68 and 82 abutting so that the cap 70 is locked to the hub 18.

For ease of packaging, it is preferred that the feet 86, 88, 90 be attached to the main body of the cap 70 at the closed end 84 by means permitting the feet to be resiliently squeezed together to fit within the cross sectional envelope of the cap. Thus, the feet may be connected to the cap body by "living hinges" 92, 94, 96, a living hinge being notoriously well known to be a flexible plastic hinge formed at the junction between two elements of the same material but reduced in cross section so that one element may flex or pivot relative to the other. Thus, the cap and the feet, may be formed from any conventional synthetic plastic material such as polyethylene or other plastics now commonly used for protective caps, the junction between the feet and the body of the cap being of reduced cross section so that the feet can be folded relative to each other and to the body of the cap. Accordingly, the feet may be folded inwardly when the syringe is packaged and will flex partially outwardly to the operative extended position when unpacked. The feet may thus act to stand the cap on its end, and when the needle and hub are inserted into the cap, any additional spreading of the feet which may occur would not then hinder the use; once the needle 16 and hub is within the cap the closed end 84 may then act as an abutment against the surface of the table or the like when the syringe is pushed downwardly to ensure that the cap is properly locked to the hub. This may readily be performed by the user with only one hand.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A disposable syringe comprising a barrel having a hollow interior, a first end and a second end, a plunger extending through said first end and slidably disposed within said hollow interior, a hollow needle, a hub connected to said needle and to said second end for attaching said needle to said barrel with the interior of said needle in flow communication with the interior of said barrel, said hub having a peripheral surface intermediate said second end and said needle, a flange extending outwardly from said peripheral surface, said flange having a wall substantially normal to said surface facing said second end and a forward facing wall inclined relative to said surface converging in a direction toward said needle, a protective cap having a closed end and an open end adapted to be disposed on said hub in a protective position over said needle, said cap having an annular skirt at said open end having an inclined interior surface converging toward said closed end for snugly receiving and being removeably attached to said facing wall of said flange when said cap is positioned on said hub, an annular locking flange formed on said cap spaced from said skirt, said locking flange having an internal configuration of substantially the same configuration and size as the flange on said hub for receiving and locking about the flange on said hub when said cap and hub are pushed relatively toward each other and said skirt is forced past the flange on said hub, and support means at said closed end for supporting said cap on a planar surface.

2. A disposable syringe as recited in claim 1, wherein said support means comprises a plurality of feet extending outwardly and away from said closed end at an inclination relative to each other.

3. A disposable syringe as recited in claim 2, wherein said feet are integral with and resiliently joined to said cap, thereby permitting said feet to be folded inwardly toward each other.

4. The combination of a needle and a protective cap for use with a syringe having a barrel including a hollow interior, a first end and a second end, a plunger extending through said first end and slidably disposed within said hollow interior, said needle having a hollow interior, a hub secured to said needle and connected to said second end for attaching said needle to said barrel with the interior of said needle in flow communication with the interior of said barrel, said hub having a peripheral surface intermediate said second end and said needle, a flange extending outwardly from said peripheral surface, said flange having a wall substantially normal to said surface facing said second end and a forward facing wall inclined relative to said surface converging in a direction toward said needle, said protective cap having a closed end and an open end adapted to be disposed on said hub in a protective position over said needle, said cap having an annular skirt at said open end having an inclined interior surface converging toward said closed end for snugly receiving and being removeably attached to said forward facing wall of said flange when said cap is positioned on said hub, an annular locking flange formed on said cap spaced from said skirt, said locking flange having an internal configuration of substantially the same configuration and size as the flange on said hub for receiving and locking about the flange on said hub when said cap and hub are pushed relatively toward each other and said skirt is forced past the flange on said hub, and support means at said closed end for supporting said cap on a planar surface.

5. The combination of a needle and a protective cap as recited in claim 4, wherein said support means comprises a plurality of feet extending outwardly and away from said closed end at an inclination relative to each other.

6. The combination of a needle and a protective cap as recited in claim 5, wherein said feet are integral with and resiliently joined to said cap, thereby permitting said feet to be folded inwardly toward each other.

7. The combination of a needle and a protective cap for use with a syringe having a barrel including a hollow interior, a first end and a second end, a plunger extending through said first end and slidably disposed within said hollow interior, said needle having a hollow interior, a hub secured to said needle and connected to said second end for attaching said needle to said barrel with the interior of said needle in flow communication with the interior of said barrel, said hub having a peripheral surface intermediate said second end and said needle, cap securing means on said peripheral surface, said protective cap having a closed end and an open end adapted to be disposed on said hub in a protective position over said needle, said cap having annular skirt means at said open end for snugly receiving and being removeably attached to said cap securing means when said cap is positioned on said hub, annular locking means formed on said cap spaced from said skirt, said locking means having an internal configuration for cooperating with said cap securing means for receiving and locking to said cap securing means when said cap and hub are pushed relatively toward each other and said skirt is forced past the cap securing means on said hub, and support means comprising a plurality of feet at said closed end, said feet extending outwardly and away from said closed end at an inclination relative to each other for supporting said cap on a planar surface.

8. The combination of a needle and a protective cap as recited in claim 7, wherein said feet are integral with and resiliently joined to said cap, thereby permitting said feet to be folded inwardly toward each other.

* * * * *